United States Patent
Honma et al.

(10) Patent No.: US 8,029,990 B2
(45) Date of Patent: Oct. 4, 2011

(54) CELL TRANSFECTION ARRAY FOR INTRODUCTION OF NUCLEIC ACID

(75) Inventors: Kimi Honma, Tokyo (JP); Takahiro Ochiya, Tokyo (JP)

(73) Assignee: Koken Co., Ltd., Tokyo (JP)

( * ) Notice: Subject to any disclaimer, the term of this patent is extended or adjusted under 35 U.S.C. 154(b) by 481 days.

(21) Appl. No.: 11/996,002

(22) PCT Filed: Jul. 22, 2005

(86) PCT No.: PCT/JP2005/013500
§ 371 (c)(1),
(2), (4) Date: Mar. 12, 2008

(87) PCT Pub. No.: WO2007/010620
PCT Pub. Date: Jan. 25, 2007

(65) Prior Publication Data
US 2009/0093058 A1    Apr. 9, 2009

(51) Int. Cl.
*C12Q 1/68*    (2006.01)
(52) U.S. Cl. .............................. 435/6; 435/325; 435/375
(58) Field of Classification Search .................... None
See application file for complete search history.

(56) References Cited

U.S. PATENT DOCUMENTS

| 6,998,268 B2 * | 2/2006 | Terada et al. .................. 435/455 |
| 2004/0266004 A1 * | 12/2004 | Terada et al. .................. 435/455 |

FOREIGN PATENT DOCUMENTS
WO    WO 03/000297    1/2003

OTHER PUBLICATIONS

Ochiya et al. Biomaterials for Gene Delivery: Atelocollagen-mediated controlled release of molecular medicines. Current Gene Therapy 2001, vol. 1:31-52.*

Steve Bailey, et al., "Applications of transfected cell microarrays in high-throughput drug discovery" Drug Dicove. Today., 2002, vol. 7 S113-118.
Cohen-Sacks et al., "Delivery and expression of pDNA embedded in collagen matrices" J. Control Release, 2004, vol. 95, pp. 309 to 320.
Vancha et al., "Use of polyethyleneimine polymer in cell culture as attachment factor and lipofection enhancer," BMC Biotechnol., 2004, vol. 4, pp. 23.
Homka et al., "The role of atelocollagen-based cell transfection array in high-throughput screening of gene functions and in drug discovery," Current Drug Discovery Technologies, Bentham Science Publishers, NL, 1 (4):287-294, Dec. 1, 2004.
Junald Ziauddin and David M. Sabatini, "Microarrays of cells expressing defined cDNAs," Nature 411, 107, May 2001.
Honma et al, "Atelocollagen-based Gene Transfer in Cells Allows High-Throughput Screening of Gene Functions," Biochemical and Biophysical Research Communications 289, 1075-1081 (2001).
Takeshita and Ochiya, "Atelocollagen-mediated controlled release of molecular medicines," Molecular Medicine, Feb. 2005, vol. 42, pp. 292 to 297, Abstract only.

* cited by examiner

*Primary Examiner* — Kimberly Chong
(74) *Attorney, Agent, or Firm* — Joseph Hyosuk Kim; JHK Law

(57) ABSTRACT

The subject of the present invention is to provide a microarray for introducing nucleic acid, the microarray capable of introducing and expressing nucleic acid into cells simply by adding the nucleic acid onto a plate and the like, and then seeding the cells thereon and culturing them without adding a nucleic acid-introducing reagent or additives. The subject is achieved by preparing the microarray including atelocollagen, a gene-introducing agent and nucleic acid on a plate and the like for the introduction of nucleic acid. The nucleic acid can be introduced into a cell by seeding cells into which nucleic acids are introduced on the microarray and culturing them without the need of preparing a mixture of viral vectors, nucleic acids and a nucleic acid-introducing agent after culturing cells or the need of adding a nucleic acid-introducing agent and additives.

10 Claims, 6 Drawing Sheets

EFFECTS OF ATELOCOLLAGEN ON THE CELL GROWTH OF MCF-7 CELLS SUBJECTED TO TRANSFECTION.

THE ADDITION OF ATELOCOLLAGEN RESULTED IN KEEPING A STRONG GENE EXPRESSION EVEN 7 DAYS AFTER TRANSFECTION.

CELL TRANSFECTION ARRAY FOR INTRODUCTION OF NUCLEIC ACID

TECHNICAL FIELD

The present invention relates to a novel cell transfection array for introduction of nucleic acid, and more specifically to a cell transfection array for the introduction of nucleic acid using a collagen.

BACKGROUND ART

Introduction of nucleic acid (transfection) into a cell of a potential host, which is one of approaches for genetic research, is a useful method to analyze gene function. In particular, the observation of changes in cell function after gene expression or after inhibiting the expression of genes has been conducted by introducing plasmid DNAs, viral vectors, antisense oligonucleotides, siRNAs and the like into cells. As of now various kinds of genomes have been decoded, and technologies to analyze those gene functions at the cell level attract the attention in genetic research. The development of apparatus to analyze cell function, for example, recent multi-imaging analyzers and plate readers provide short time analysis of cell function of multiple samples cultured in multi-well plates, so that the cell level analysis of gene function combining the transfection of nucleic acid with apparatus for analyzing cell function is increasing its importance.

However, the conventional methods for introducing nucleic acid is conducted by seeding cells in a culture container, culturing them and then infecting them with viral vectors into which the nucleic acid to be introduced have been integrated, or by mixing the nucleic acid with an introducing agent and adding the mixture into a culture medium, thus the preparation step of the mixture of viral vectors or nucleic acid with an introducing agent is needed each time, making the methods complicated and exceedingly laborious especially in a case introducing nucleic acid of multiple samples from diverse kinds. Further, there has been a problem in those methods that cell function can not be accurately determined due to the cytotoxicity of viruses or introducing agents, which interfere with, for example, cell growth and apoptosis assays.

Accordingly, a transfection method has been developed, wherein genes are placed on a slide glass in advance, an introducing agent is added at the time of use and then cells are seeded there (Non-patent document 1).

Further, a gene screening method based on changes in cell function has been reported, wherein the changes are presented by facilitation or inhibition of the gene expression, using a cell transfection array in which plates are precoated with the mixture of atelocollagen and nucleic acid (Non-patent document 2, patent document 1). (Non-patent document 1) Nature 411, 107, 2001 (Non-patent document 2) Biochemical and Biophysical Research Communications 289, 1075-1081 (2001) (Patent document 1) Pamphlet of International Publication WO 03/000297

DISCLOSURE OF THE INVENTION

Problem to be Solved

The subject of the present invention is to provide a cell transfection array for introduction of nucleic acid in introducing a gene into a cell, wherein the array allows nucleic acid to be introduced into a cell and effectively expressed simply by seeding cells on a solid-phase including the desired nucleic acid and culturing them.

Means to Solve the Problems

The present inventor strenuously studied to solve the matters above, finally found that before cell culturing, the use of a cell transfection array including a collagen, a nucleic acid-introducing agent and the desired nucleic acid on a solid-phase enables nucleic acid to be introduced into a cell without the step of adding a viral vector, nucleic acid, a nucleic acid-introducing agent and the like into the cultured cells after cell culturing, and thus completed the present invention.

The present invention consists of the following:
1. A cell transfection array for introduction of nucleic acid, comprising atelocollagen, a nucleic acid-introducing agent and nucleic acid.
2. The cell transfection array for cell introduction according to the preceding aspect 1, comprising atelocollagen in an amount capable of decreasing cytotoxicity.
3. The cell transfection array according to the preceding aspect 1 or 2, wherein the nucleic acid-introducing agent is any one selected from liposome or non-liposomal lipid, viral vector, DEAE dextran, calcium phosphate or dendrimer.
4. The cell transfection array according to any one of the preceding aspects 1 to 3, wherein the nucleic acid-introducing agent is liposome.
5. The cell transfection array according to any one of the preceding aspects 1 to 4, wherein the nucleic acid is plasmid DNA, polynucleotide, oligonucleotide, ribozyme or siRNA.
6. A method for preparing the cell transfection array according to any one of the preceding aspects 1 to 5.
7. A kit for preparing the cell transfection array according to any one of the preceding aspects 1 to 5.
8. A method for introducing nucleic acid into a cell using the cell transfection array according to any one of the preceding aspects 1 to 5.
9. A method for introducing nucleic acid into a cell, comprising seeding cells on the cell transfection array according to any one of the preceding aspects 1 to 5.
10. A method for introducing nucleic acid into a cell comprising the steps of preparing a cell transfection array for introduction of nucleic acid, including atelocollagen, a nucleic acid-introducing agent and nucleic acid and seeding cells on the cell transfection array.
11. The method for introducing nucleic acid into a cell according to the preceding aspect 10, comprising the steps of preparing a cell transfection array for introduction of nucleic acid including atelocollagen in an amount capable of decreasing cytotoxicity and seeding cells on the cell transfection array.
12. The method for introducing nucleic acid according to the preceding aspect 10 or 11, wherein the nucleic acid-introducing agent is any one selected from liposome or non-liposomal lipid, viral vector, DEAE dextran, calcium phosphate or dendrimer.
13. The method for introducing nucleic acid according to the preceding aspect 12, wherein the nucleic acid-introducing agent is liposome.
14. The method for introducing nucleic acid according to any one of the preceding aspects 10 to 13, wherein the nucleic acid is plasmid DNA, polynucleotide, oligonucleotide, ribozyme or siRNA.
15. A nucleic acid introduction kit comprising the cell transfection array according to any one of the preceding aspects 1 to 5.

Effects of the Invention

The present invention may permit genes to express for a long time in a state keeping an effective and appropriate introduction of nucleic acid and a decreased cytotoxicity and further permit cell transfection array for introduction of nucleic acid to be stored for a long time in a state keeping nucleic acid introducible. Further, the culture environment of the cell transfection array for introduction of nucleic acid of the present invention (hereinafter sometimes simply referred to as "cell transfection array") is separated into different nucleic acid groups, so that extracellular environments can be assessed, like the situation where changes in materials secreted from cells, into which different nucleic acids are introduced, can be measured by collecting each culture medium. Further, conventionally used multi-well plates can be used in the cell transfection array as a base, thus there is an advantage of using them for existing reagents and apparatus for analyzing cell function.

DESCRIPTION OF THE PREFERRED EMBODIMENT

Figure 1:
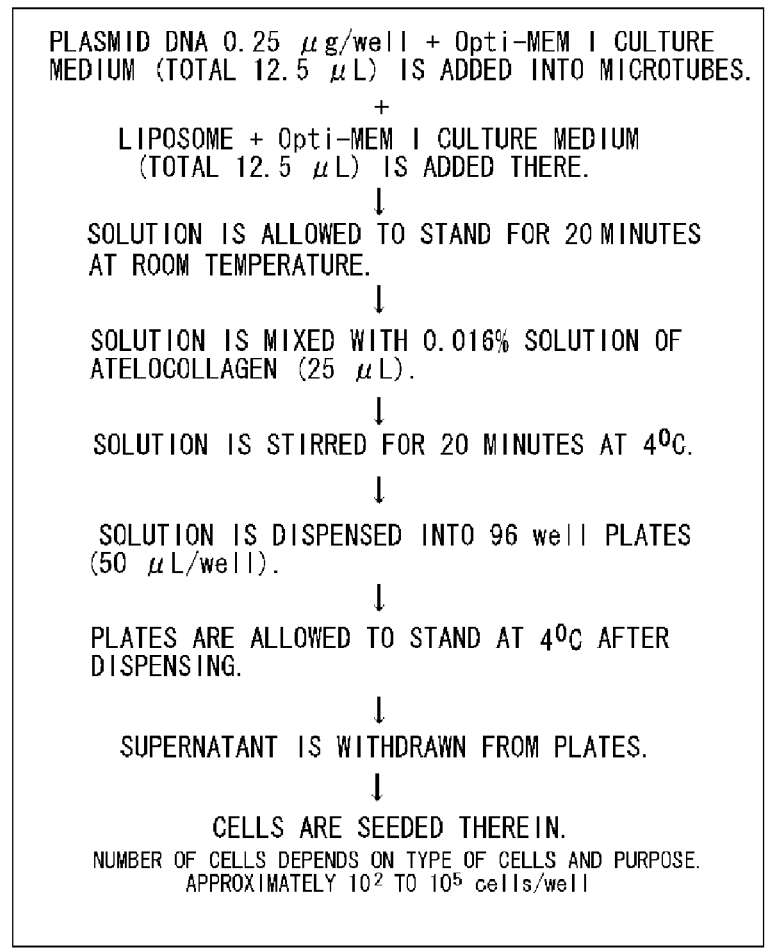
FIG. 1 shows a method for preparing a cell transfection array of the present invention. (Example 1)

There is no restriction to the types of nucleic acid which can be comprised in the cell transfection array of the present invention and introduced into a cell, and any nucleic acid, which may be the single or double stranded or their relatives, in particular, plasmid DNAs, polynucleotides, oligonucleotides, ribozymes and small interfering RNAs (siRNAs) can be used.

If nucleic acid for use in the present invention is double-stranded DNA or RNA, it may be either in straight or cyclic form. Further, nucleic acid comprising the desired sequence may be integrated into a vector or be in the form of a plasmid. The plasmid of interest may be for either expression or non-expression.

If the nucleic acid for use in the present invention is oligonucleotide, there is no restriction to the types of oligonucleotide to be introduced, and any of single or double stranded oligonucleotides or their relatives can be used. In particular, deoxyribonucleotides (DNAs), ribonucleotides, 2-O(2-methoxy)ethyl-modified nucleic acid (2'-MOE-modified nucleic acid), siRNAs, crosslinked nucleic acid (Locked Nucleic Acid: LNA; Singh, et al., Chem. Commun., 455 (1998)), peptide nucleic acids (Peptide Nucleic Acid: PNA; Nielsen, et al., Science, 254, 1497, 1991) or morpholino antisense nucleic acids (Morpholino antisense; Sumerton and Weller, Antisense & Nucleic Acid Drug Development, 7, 187, 1997) can be mentioned.

A nucleic acid-introducing agent for use in the present invention can be those well known per se, and in particular, it may be liposome, non-liposomal lipid, viral vector, DEAE dextran, calcium phosphate, dendrimer, and the like, and preferably it is liposome, and more preferably cationic liposome can be used.

The amount of a nucleic acid-introducing agent for use can be selected as appropriate in relation to the amount of collagen used. In particular, the solution of a nucleic acid-introducing agent can be used at a concentration in the range between 0.01 ng/mL and 100 ng/mL, and preferably between 0.1 ng/mL and 50 ng/mL. For example, if a commercially available nucleic acid-introducing agent is used, it can be used in an amount ranging from 1/1 to 1/100 and preferably from 1/2 to 1/50 of the amount specified in the instruction manual for use of the nucleic acid-introducing agent.

A collagen for use in the present invention is preferably atelocollagen, and there is no restriction to its kind, origin, type and the like. As a kind, an enzyme-solubilized collagen (Atelocollagen) and its modified forms can be mentioned. As a modified form, those having a chemical modification of an amino group or carboxyl group on its side chain and those of the chemically or physically crosslinked can be used. Further, referring to origin, though any collagen derived from mammals such as bovine, swine, horse and human; bird and fish can be used, the collagen should preferably show heat stability and no change at a temperature for culturing cells. In particular, not only collagens from mammals and birds, but also collagens transgenically obtained from them are desired. Referring to the types of collagen, there is no restriction in particular, and Types I, II and III are useful because of its easy access.

The collagen can be used in an amount capable of decreasing toxicity to cells. There is anxiety, for example, for possible toxicity of a nucleic acid-introducing agent to cells. In particular, the collagen solution can be used at a concentration ranging from 0.00001 to 3% (0.0001 to 30 mg/mL), preferably from 0.0001 to 0.1% and more preferably from 0.0005 to 0.05%.

The concentration of nucleic acid in a mixture solution of a collagen, a nucleic acid-introducing agent and nucleic acid may be in the range from 0.001 to 1000 μg/mL, preferably from 0.01 to 200 μg/mL and more preferably 0.05 to 100 μg/mL.

The cell transfection array of the present invention can be prepared by mixing the nucleic acid described above and a nucleic acid-introducing agent in collagen and placing it on a solid-phase support. Though any order and any ratio can be taken for mixing collagen solution, nucleic acid-introducing agent and nucleic acid, the collagen solution is preferably added to the solution after mixing nucleic acid and a nucleic acid-introducing agent. A solution comprising nucleic acid and a nucleic acid-introducing agent and a collagen solution can be mixed at a ratio ranging from 1:99 to 99:1, preferably from 10:90 to 90:10 and more preferably from 30:70 to 70:30.

The cell transfection array of the present invention can use a solid-phase support capable of culturing cells. Namely, any solid-phase support can be used as long as it will not kill cells and not inhibit the incorporation of nucleic acid into cells in the present introduction method of nucleic acid. Further, the solid-phase support preferably has sectioned culture environments for respective different nucleic acids and specifically, cell culture plates can be used. More preferably, commercially available cell culture plates having wells can be used, where culture environment is sectioned into, for example, 6-well, 24-well, 48-well, 96-well, 384-well and 1536-well.

In the preparation of the cell transfection array of the present invention, if the cell culture plate described above is used, the mixture of a collagen, a nucleic acid-introducing agent and nucleic acid can be added to each well to load at a volume ranging from 0.1 to 3000 μL/cm², and preferably 1 to 1500 μL/cm².

In order to provide the cell transfection array of the present invention comprising a collagen, a nucleic acid-introducing agent and nucleic acid, the mixture of nucleic acid and a nucleic acid-introducing agent can be added into a collagen solution, and then thus obtained mixture is added into plates, or the mixture solution of a nucleic acid-introducing agent and a collagen can be combined with nucleic acid, and then thus obtained mixture is added into plates. Alternatively, after adding nucleic acid and a nucleic acid-introducing agent into a mixing plate, a collagen solution can be added thereto. The step by mixing nucleic acid and a nucleic acid-introducing agent, allowing it to stand for a while at room temperature, then mixing a collagen solution therewith, and adding it into plates is preferred.

The cell transfection array of the present invention can be prepared either step by adding the mixture of the nucleic acid to be introduced, a nucleic acid-introducing agent and a collagen into a solid-phase support such as plates and drying it or by allowing nucleic acid, a nucleic acid-introducing agent and a collagen adhered onto a plate to skip drying step.

Seeding and culturing cells on the cell transfection array prepared as described above provides transgenic cells. Any type of cell can be used as long as it is a potential host for the desired gene and, for example, yeasts, animal cells, insect cells and plant cells can be used. As cells to add, for example, those prepared in a 96-well microplate at 10 to $10^6$ cells/well and preferably $10^2$ to $10^5$ cells/well can be used using a widely known culture medium for cell culturing.

The present invention relates to the cell transfection array described above, a method for the preparation thereof, the above-described introduction method of nucleic acid using the cell transfection array and an introduction method of nucleic acid comprising the cell transfection array of the present invention. Further, the present invention covers a kit for preparing the cell transfection array, comprising a nucleic acid-introducing agent and a collagen and further a nucleic acid introduction kit comprising the cell transfection array described above.

EXAMPLE

To gain a better understanding of the present invention, the invention is described in detail below with reference to Examples and Experimental Examples, but it is clear that the present invention will not be limited by these Examples.

Example 1

Preparation of Cell Transfection Array

1) Material

Plasmid DNA was used as nucleic acid (gene) and pEGFP-N1 (supplied by Clonetech) which expresses enhanced green fluorescent protein (EGFP) was also used. As a nucleic acid-introducing agent, Lipofectamine 2000 (supplied by Invitrogen, hereinafter simply referred to as LF or LF2000), a commercially available agent comprising cationic liposome, was used.

2) Method

Cell transfection arrays were prepared according to a flow chart in FIG. 1. In principle, the cell transfection array is the one obtained by adding the mixture of plasmid DNA (nucleic acid), LF2000 (nucleic acid-introducing agent) and atelocollagen (collagen) into a 96-well microplate as illustrated in FIG. 1. In the following Experimental Examples, effects on cell growth, transfection, gene expression and the like were examined by changing microplate-adding condition in various ways.

Experimental Example 1

Observation of Transfection Efficiencies by Changing the Amount of the Nucleic Acid-Introducing Agent for Use Cell transfection arrays were prepared according to the method of Example 1 using systems with various amounts of LF2000. Genes were introduced into PC12 cells (cells derived from rat adrenal pheochromocytoma) on the cell transfection array, and effects on cells and transfection efficiencies were observed.

PC12 cells were grown using a culture medium of DMEM supplemented with 10% horse serum and 5% fetal bovine serum (FBS), prepared into a cell count of $2 \times 10^5$ cells/ml, then seeded at 100 μL/well and cultured for three days.

The introduction of genes into cells was confirmed by observation of fluorescence due to the expression of enhanced green fluorescent protein (EGFP) in the cells. The transfection efficiency was indicated as the ratio of EGFP-expressed cells to total number of cells in a particular visual field.

Figure 2:
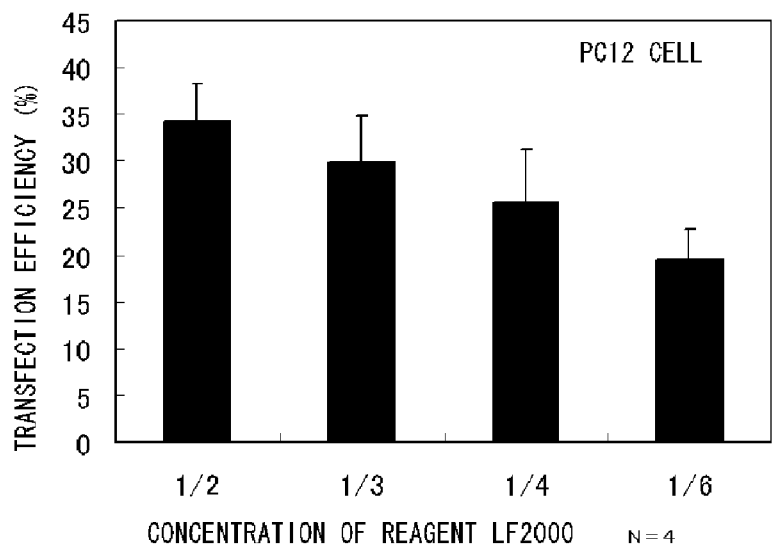
FIG. 2 shows transfection efficiencies into PC12 cells wherein the concentration of a nucleic acid-introducing agent to be added is varied in the preparation of the cell transfection array of the present invention. (Experimental Example 1)
Figure 3:
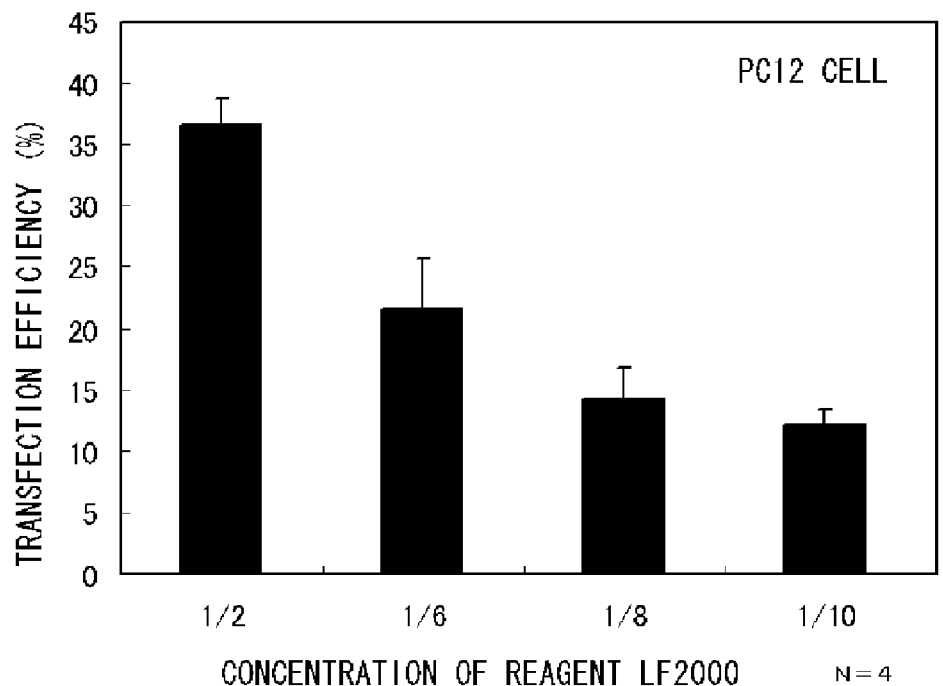
FIG. 3 shows transfection efficiencies into PC12 cells wherein the concentration of a nucleic acid-introducing agent to be added is varied in the preparation of the cell transfection array of the present invention. (Experimental Example 1)

The reagent LF2000 should be used in an amount of 0.8 μg/well according to the attached instruction. However, when the transfection efficiencies were tested by changing the amount of use from ½ to ¹⁄₁₀ of that, the amount of use-dependent transfection efficiencies of LF2000 were observed as shown in FIGS. 2 and 3, while when the amount of use of LF2000 was at ¼ or more, approximately 25% or more transfection efficiencies, which are equivalent to that of conventional introduction methods of nucleic acid, were observed.

Experimental Example 2

Observation of Transfection Efficiencies by Changing the Amount of the Nucleic Acid-Introducing Agent for Use Cell transfection arrays were prepared according to the method of Example 1, using systems with various amounts of LF2000. Genes were introduced into 293 cells on the cell transfection array, and transfection efficiencies were observed.

293 cells (cells from human embryonic kidney; cells transformed with adenovirus) were grown using a culture medium of DMEM supplemented with 10% fetal bovine serum (FBS), prepared into a cell count of $2\times10^5$ cells/ml, then seeded at 100 µL/well and cultured for three days. The measurement of transfection efficiencies was conducted in the same manner as in Experimental Example 1.

Figure 4:
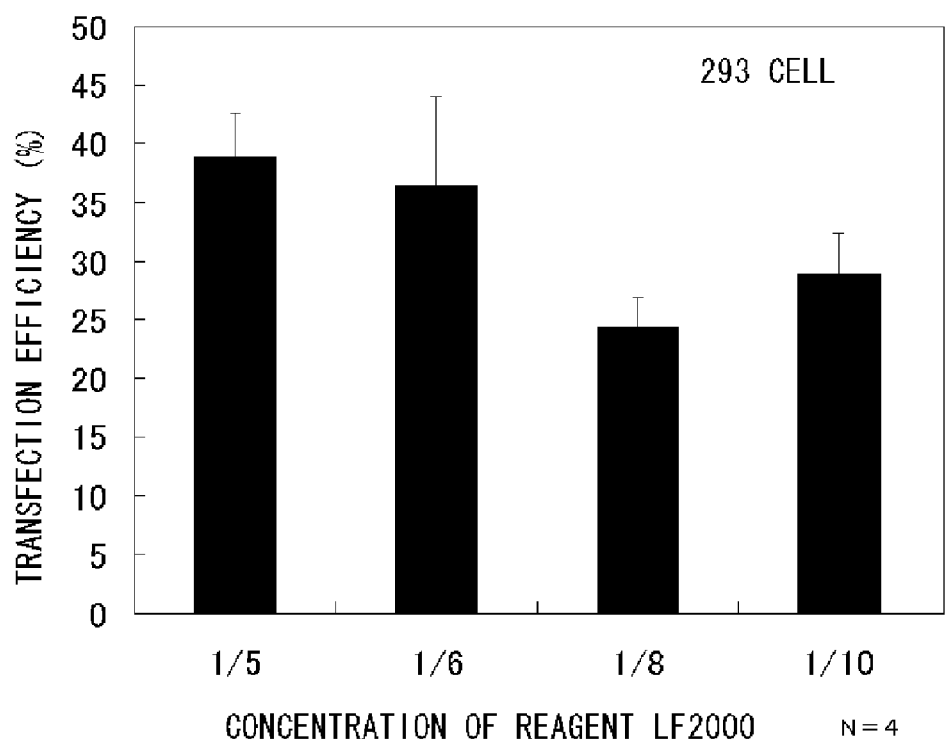
FIG. 4 shows transfection efficiencies into 293 cells wherein the concentration of a nucleic acid-introducing agent to be added is varied in the preparation of the cell transfection array of the present invention. (Experimental Example 2)

Transfection efficiencies were observed by changing the amount of reagent LF2000 used from 1/5 to 1/10, and as seen in FIG. 4, when the amount of use of reagent LF2000 was at an amount of 1/6 or more, 35% or more steady transfections were observed.

Experimental Example 3

Observation of Transfection Efficiencies by Changing the Amount of a Nucleic Acid-Introducing Agent for Use Cell transfection arrays were prepared according to the method of Example 1, using systems with various amounts of LF2000. Genes were introduced into MCF-7 cells (cells derived from human breast cancer) seeded on the cell transfection array, and effects on cells and transfection efficiencies were observed when genes were introduced.

MCF-7 cells were grown using a culture medium of RPMI media supplemented with 10% fetal bovine serum, prepared into a cell count of $2\times10^4$ cells/ml, then seeded at 100 µL/well and cultured for five days.

Cell growth rate was measured by adding 10 µL of Tetra color one proliferation assay reagent into each well, incubating them in a $CO_2$ incubator for an hour at 37° C. and measuring absorbance at a wavelength of 450 nm (O.D. 450) using an absorbance at a wavelength of 630 nm (O.D. 630) as a control. Transfection efficiencies were measured in the same manner as in Experimental Example 1.

Figure 5:
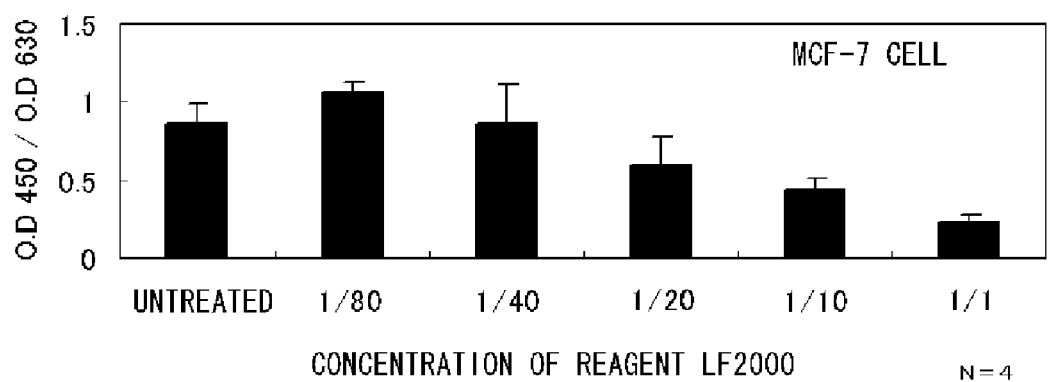
FIG. 5 shows the proliferation of transgenic cells of MCF-7 cells wherein the concentration of a nucleic acid-introducing agent to be added is varied in the preparation of the cell transfection array of the present invention. (Experimental Example 3)

The result of above showed that decreased cytotoxicity was obtained when LF2000 was used in an amount less than 1/40 of that recommended in the attached instruction (FIG. 5). Further, transfection effects were observed when 1/40 of the amount was used (Table 1).

Thus, the decreased cytotoxicity and transfection effects were observed by using a cell transfection array comprising the nucleic acid-introducing agent of LF2000 in an amount 1/40 of that recommended in the attached instruction.

TABLE 1

| | AMOUNT OF LF2000 USED | | | | | |
| --- | --- | --- | --- | --- | --- | --- |
| | UNTREATED | 1/80 | 1/40 | 1/20 | 1/10 | 1/1 |
| TRANSFECTION EFFICIENCY (%) | 0 | 2.3 | 11.9 | 28.3 | 12.4 | 29.4 |

Experimental Example 4

Effects of the Presence or Absence of Atelocollagen on Cells and Expression Efficiencies Cell transfection arrays of systems with or without atelocollagen were prepared according to the method of Example 1, using LF2000 in an amount 1/40 of that recommended in the attached instruction. MCF-7 cells seeded on the cell transfection array in the same manner as in Experimental Example 3, and effects of the presence or absence of collagen on cells were examined in cases where genes were introduced. Cell growth rates were measured in the same manner as in Experimental Example 3, and the method for measuring transfection efficiencies was the same as in Experimental Example 1.

Figure 6:
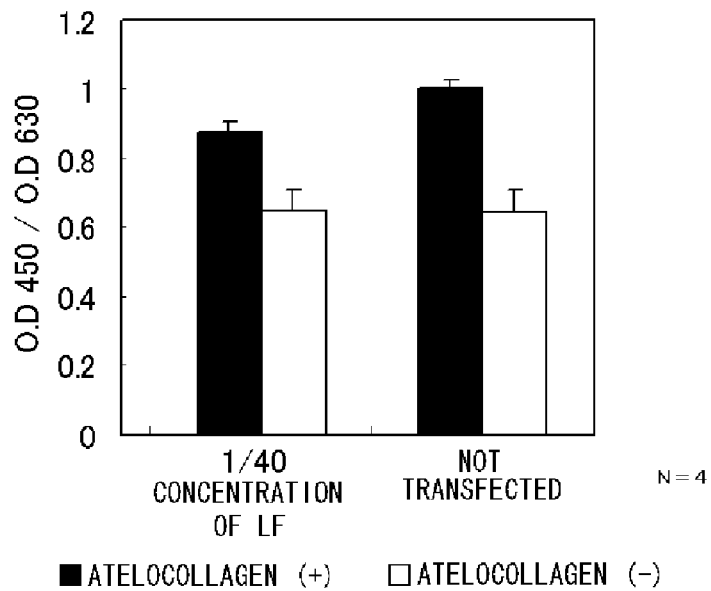
FIG. 6 shows the effects of presence or absence of collagen on cell growth in the preparation of the cell transfection array of the present invention. (Experimental Example 4)
Figure 7:
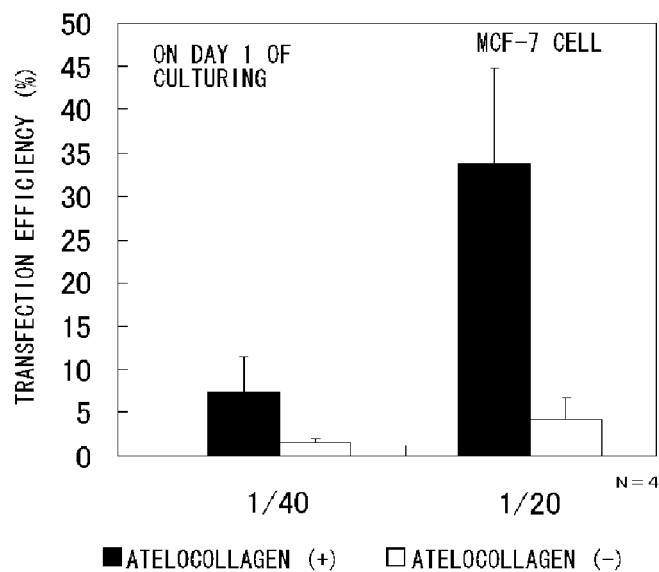
FIG. 7 shows the effects of presence or absence of collagen on transfection efficiency in the preparation of the cell transfection array of the present invention. (On day 1 of culturing) (Experimental Example 4)
Figure 8:
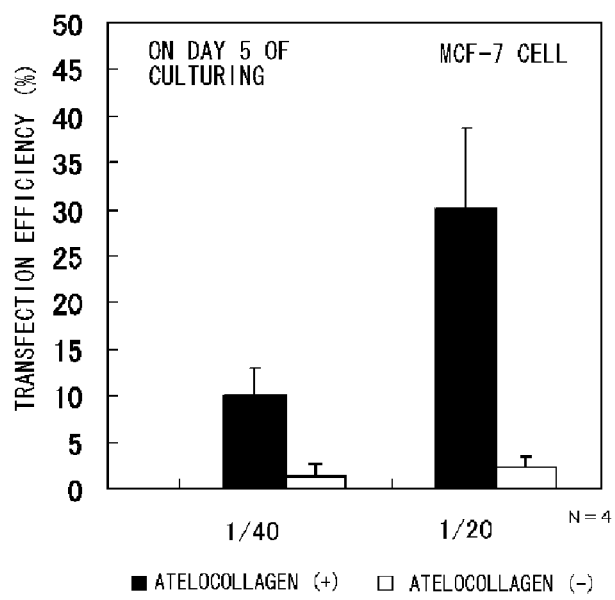
FIG. 8 shows the effects of presence or absence of collagen on transfection efficiency in the preparation of the cell transfection array of the present invention. (On day 5 of culturing) (Experimental Example 4)

The result of above showed that good cell growth and decreased cytotoxicity were observed when cells were seeded on the cell transfection array with Atelocollagen (FIG. 6). Further, the introduction of genes into cells was observed with the cell transfection array prepared using LF2000 in an amount of 1/20 and 1/40. Further, higher effects were shown with systems to which atelocollagen was added on both day 1 and day 5 of culturing (FIGS. 7 and 8).

Thus, it was confirmed that high transfection effects can be obtained by using the cell transfection array to which atelocollagen was added.

Experimental Example 5

Effects of the Presence or Absence of Atelocollagen on Cells and Introduction Efficiencies Cell transfection arrays were prepared according to the method of Example 1 with systems with or without atelocollagen using LF2000 in an amount 1/4 of that recommended in the attached instruction. PC12 cells were seeded on the cell transfection array in the same manner as in Experimental Example 1 and cultured for three days. Effects of the presence or absence of collagen on cells were examined in cases where genes were introduced or not. Transfection was measured by the method similar to that of Experimental Example 1.

Figure 9:
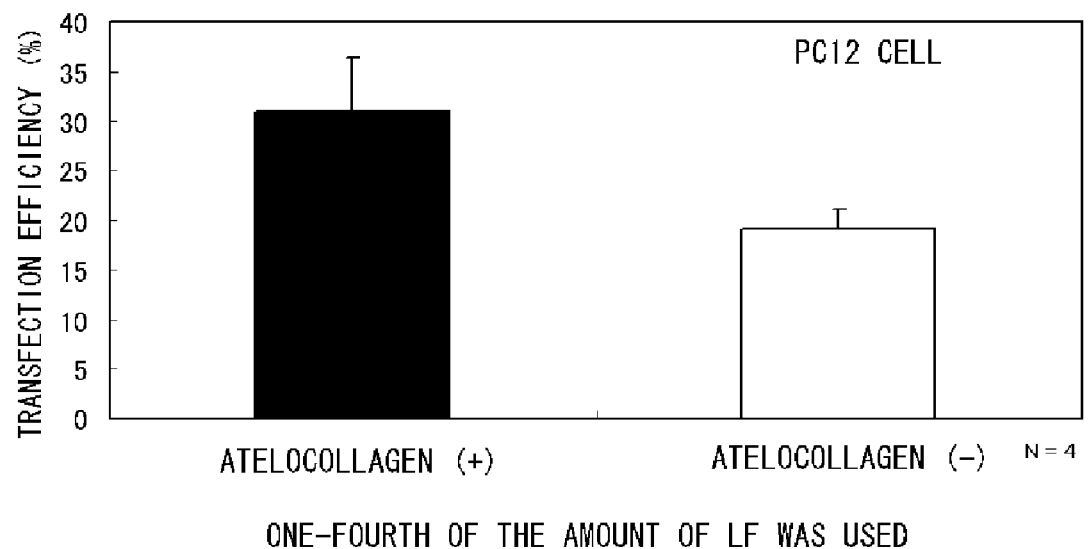
FIG. 9 shows the effects of presence or absence of collagen on transfection efficiency in the preparation of the cell transfection array of the present invention. (Experimental Example 5)

The result of above showed that when cells were seeded on the cell transfection array described above, a high transfection was observed in the system to which atelocollagen was added on day 3 of culturing (FIG. 9). Thereby, it was confirmed that high transfection effects can be obtained by using the cell transfection array to which atelocollagen was added.

Experimental Example 6

Effects of the Presence or Absence of Atelocollagen on Cells

Cell transfection arrays were prepared according to the method of Example 1, using LF2000 which was diluted at a dilution rate 2 times that recommended for use in the attached instruction. HepG2 cells (cells from human liver cancer) were grown on the cell transfection array in the same manner as in Experimental Example 1 using a culture medium of DMEM supplemented with 10% fetal bovine serum, prepared into a cell count of $1\times10^5$ cells/ml, then seeded at 100 µL/well and cultured for three days. Further, as a conventional method, transfection was conducted according to the attached instruction using reagent LF2000 in an amount equal to that of the present method. The states of the cells into which genes were introduced by respective methods were microscopically observed. Transfection was confirmed by observing EGFP's expression using a fluorescence microscopy.

Figure 10:
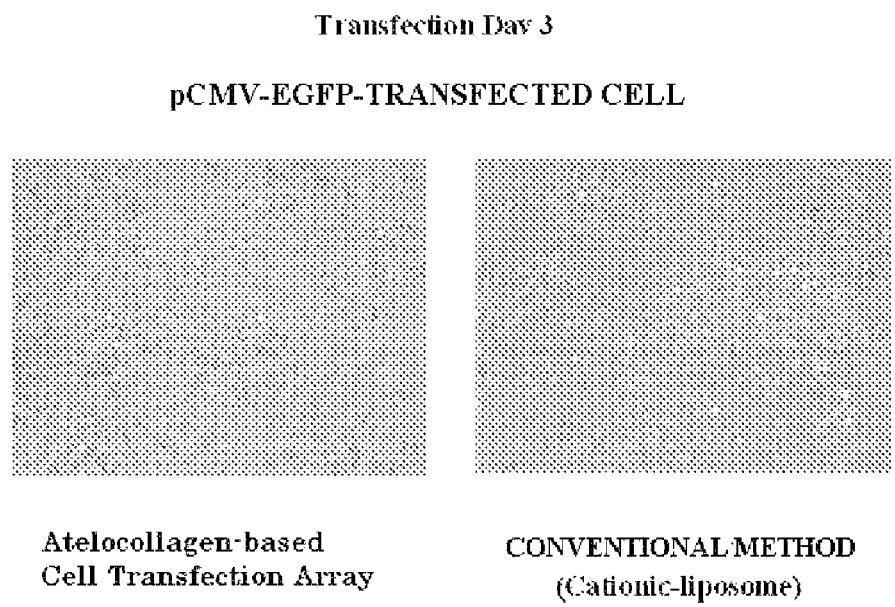
FIG. 10 shows the effects of presence or absence of collagen on cells in the preparation of the cell transfection array of the present invention. (Experimental Example 6)

The result of above showed that the decreased cytotoxicity was observed on day 3 of culturing after seeding cells on the cell transfection array described above (FIG. 10). Thereby, it was confirmed that using the cell transfection array to which atelocollagen was added leads to the decreased cytotoxicity and increased transfection effects.

Experimental Example 7

Difference of the Duration of Gene Expression in the Presence or Absence of Atelocollagen According to the method of Example 1, genes were introduced into PC12 cells in the same manner as in Experimental Example 1. The results were obtained by observing EGFP's expression using a fluorescence microscopy at 100× magnification in a time-dependent manner.

Figure 11:
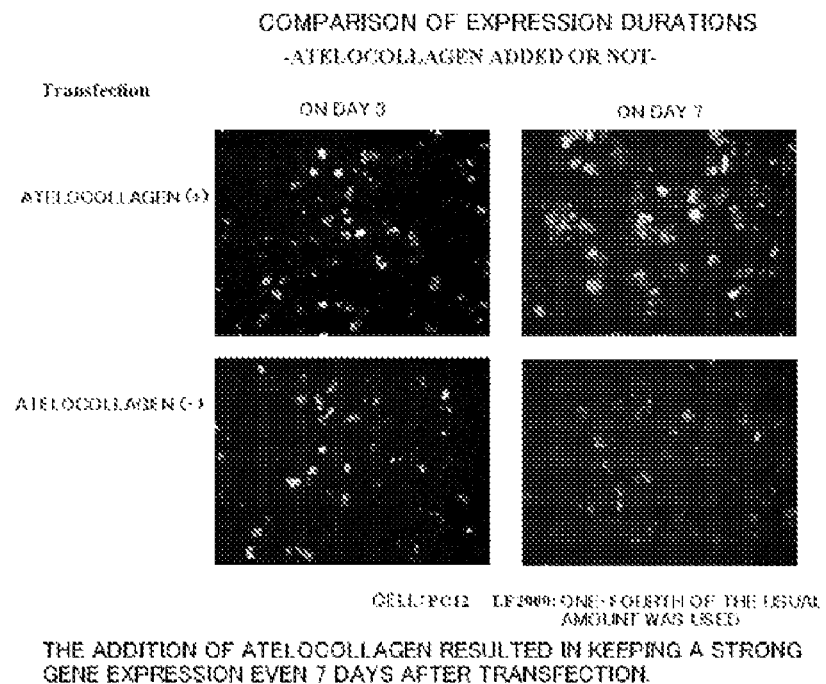
FIG. 11 shows the effects of presence or absence of collagen on the duration of gene expression in the preparation of the cell transfection array of the present invention. (Experimental Example 7)

In the results of above, after seeding cells on the cell transfection array described above, gene expression was confirmed under microscopic observation regardless of the presence or absence of atelocollagen on day 3 of culturing or later, and on day 7 of culturing EGFP's expression was sharply decreased in a system to which atelocollagen was not added, while that still maintained in a system to which atelocollagen was added, showing that the addition of atelocollagen allows genes to express for a long time (FIG. 11).

Experimental Example 8

Preservation Stability of Cell Transfection Array

According to the method of Example 1, cells were seeded immediately after the preparation of the cell transfection array and after respective hours of storage and cultured for three days, and then transfection efficiencies were examined to check preservation stability. The measurement of transfection efficiencies was conducted in the same manner as in Experimental Example 1.

Figure 12:
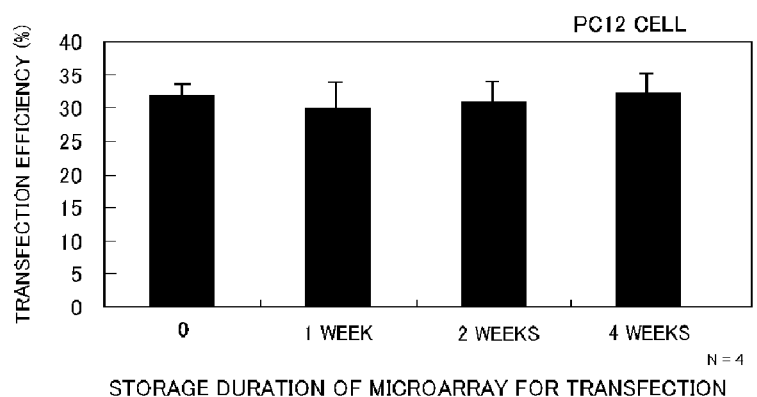
FIG. 12 shows effects on transfection efficiency using the cell transfection array immediately after the preparation and after respective hours of storage of the cell transfection array. (Experimental Example 8)

The result of above showed that the same transfection efficiency as obtained immediately after the preparation was confirmed even in four weeks after the preparation of the cell transfection array (FIG. 12). The retention of the preservation stability was proved by that fact.

INDUSTRIAL APPLICABILITY

According to the above description, the use of the cell transfection array of the present invention allows genes to be effectively expressed in a host cell with no need to add a nucleic acid-introducing agent and the like at the time of seeding cells. Further, the cell transfection arrays prepared can be stored approximately four weeks. Thereby, the cell transfection arrays can be prepared, transported and distributed. Therefore, preparing and distributing cell transfection arrays plated with a variety of nucleic acid allow users to analyze genes from multiple samples at cell level just by seeding cells on those cell transfection arrays, so that their application to the analysis of gene function in each research institute, screening in drug discoveries and examination in each clinical laboratories can be expected.

The invention claimed is:

1. A cell transfection array for introduction of nucleic acid, comprising: atelocollagen; a nucleic acid-introducing agent; and nucleic acid, wherein the nucleic acid-introducing agent is liposome, and the array comprises atelocollagen in an amount capable of decreasing cytotoxicity of the nucleic acid-introducing agent compared with cell transfection array without atellocollagen.

2. The cell transfection array according to claim 1, wherein the nucleic acid is plasmid DNA, polynucleotide, oligonucleotide, ribozyme or siRNA.

3. A method for preparing a cell transfection array according to claim 1.

4. A kit for preparing a cell transfection array according to claim 1.

5. A method for introducing nucleic acid into a cell using a cell transfection array according to claim 1.

6. A method for introducing nucleic acid into a cell, comprising seeding cells on a cell transfection array according to claim 1.

7. A method for introducing nucleic acid into a cell, comprising the steps of: preparing a cell transfection array for introduction of nucleic acid including atelocollagen, a nucleic acid-introducing agent and nucleic acid; and seeding cells on the cell transfection array, wherein the nucleic acid-introducing agent is liposome, and the array comprises atelocollagen in an amount capable of decreasing cytotoxicity of the nucleic acid-introducing agent compared with cell transfection array without atellocollagen.

8. The method for introducing nucleic acid according to claim 7, wherein the nucleic acid is plasmid DNA, polynucleotide, oligonucleotide, ribozyme or siRNA.

9. A nucleic acid introduction kit comprising a cell transfection array according to claim 1.

10. A method to reduce cytotoxicity resulting from transfection with a nucleic acid-introducing agent, comprising contacting cells with the cell transfection array according to claim 1.

* * * * *